(12) United States Patent
Sazegar et al.

(10) Patent No.: US 12,075,864 B2
(45) Date of Patent: Sep. 3, 2024

(54) SLEEP MASK ASSEMBLY

(71) Applicants: Hossein Sazegar, Houston, TX (US); Herve Chapellat, Houston, TX (US)

(72) Inventors: Hossein Sazegar, Houston, TX (US); Herve Chapellat, Houston, TX (US)

(*) Notice: Subject to any disclaimer, the term of this patent is extended or adjusted under 35 U.S.C. 154(b) by 44 days.

(21) Appl. No.: 18/071,270

(22) Filed: Nov. 29, 2022

(65) Prior Publication Data
US 2024/0172820 A1 May 30, 2024

(51) Int. Cl.
A61F 9/04 (2006.01)
A41D 13/11 (2006.01)

(52) U.S. Cl.
CPC .......... *A41D 13/1161* (2013.01); *A61F 9/045* (2013.01)

(58) Field of Classification Search
CPC  A41D 13/1184; A41D 13/1161; A41D 20/00; A61F 9/045; A61F 9/04; A61F 2007/0004; A47G 9/1045; A63B 33/002; A42B 1/22; G02C 9/04
See application file for complete search history.

(56) References Cited

U.S. PATENT DOCUMENTS

| | | | | |
|---|---|---|---|---|
| 2,305,080 A * | 12/1942 | Hemphill | ............... | A61F 9/04 2/15 |
| 4,679,263 A * | 7/1987 | Honer | ............... | A47G 9/1045 5/639 |
| 4,955,707 A * | 9/1990 | Gazeley | ............... | G02C 9/02 351/57 |
| 6,223,748 B1 * | 5/2001 | Chaves | ............... | A61F 9/04 128/857 |
| 6,651,256 B1 | 11/2003 | Swift | | |
| D812,676 S * | 3/2018 | Dolmetsch | ............... | D16/301 |
| D831,386 S | 10/2018 | Glasgow | | |
| 10,426,666 B1 | 10/2019 | Seidenfeld | | |
| D923,363 S * | 6/2021 | Brandy | ............... | D6/601 |
| 11,207,215 B2 | 12/2021 | Bamberg | | |
| 11,207,490 B1 * | 12/2021 | Fried | ............... | A61F 9/04 |
| D963,301 S * | 9/2022 | Alcedo | ............... | A47C 7/383 D2/866 |
| 2008/0216244 A1 * | 9/2008 | Minton | ............... | A47G 9/10 5/636 |
| 2010/0186145 A1 * | 7/2010 | Macy | ............... | A42B 1/0181 2/207 |
| 2011/0271421 A1 * | 11/2011 | Vahey | ............... | A42B 1/04 2/209.13 |

(Continued)

FOREIGN PATENT DOCUMENTS

WO    WO2008061505    5/2008

*Primary Examiner* — Jillian K Pierorazio

(57) ABSTRACT

A sleep mask assembly includes a sleep mask that is wearable on a user's face such that the sleep mask covers the user's eyes. The sleep mask has a face portion and a flap portion. The face portion rests against the user's face when the sleep mask is worn. The flap portion is positionable in a deployed position has the flap portion resting against the user's forehead to facilitate the user to comfortably rest their forehead against a support object when the user is sleeping in a sitting position. The flap portion is positionable in a stored position having the flap portion resting against the face portion. A pair of elastomeric straps is each coupled to the sleep mask thereby facilitating the pair of elastomeric straps to be worn around the user's head for retaining the sleep mask on the user's face.

8 Claims, 7 Drawing Sheets

(56) References Cited

U.S. PATENT DOCUMENTS

| | | | | |
|---|---|---|---|---|
| 2012/0131726 | A1* | 5/2012 | Schenk | A61F 9/04 |
| | | | | 2/173 |
| 2013/0174333 | A1* | 7/2013 | Schwartz | A63B 33/006 |
| | | | | 2/446 |
| 2013/0253257 | A1* | 9/2013 | Kalhory | A61H 39/04 |
| | | | | 600/27 |
| 2014/0215688 | A1* | 8/2014 | Vahey | A42B 1/04 |
| | | | | 2/209.3 |
| 2014/0311512 | A1* | 10/2014 | Owoc | A41D 20/00 |
| | | | | 132/200 |
| 2015/0000006 | A1* | 1/2015 | Anderson | A42B 1/006 |
| | | | | 2/173 |
| 2015/0116650 | A1* | 4/2015 | Li | G02C 7/101 |
| | | | | 351/47 |
| 2015/0351964 | A1* | 12/2015 | Schwartz | A61F 13/043 |
| | | | | 2/440 |
| 2016/0120253 | A1* | 5/2016 | Schenk | A61F 9/04 |
| | | | | 2/173 |
| 2017/0215544 | A1* | 8/2017 | Anderson | F21V 33/0008 |
| 2018/0055692 | A1* | 3/2018 | Maddie | A61F 9/045 |
| 2019/0121166 | A1* | 4/2019 | Ng | G02C 7/08 |
| 2020/0281770 | A1* | 9/2020 | Moreno | A41D 13/1184 |
| 2020/0323689 | A1* | 10/2020 | Morshed | A47G 9/1081 |
| 2021/0298959 | A1* | 9/2021 | Lombardo | A42B 1/247 |
| 2021/0393058 | A1* | 12/2021 | Alcedo | H04R 1/028 |

* cited by examiner

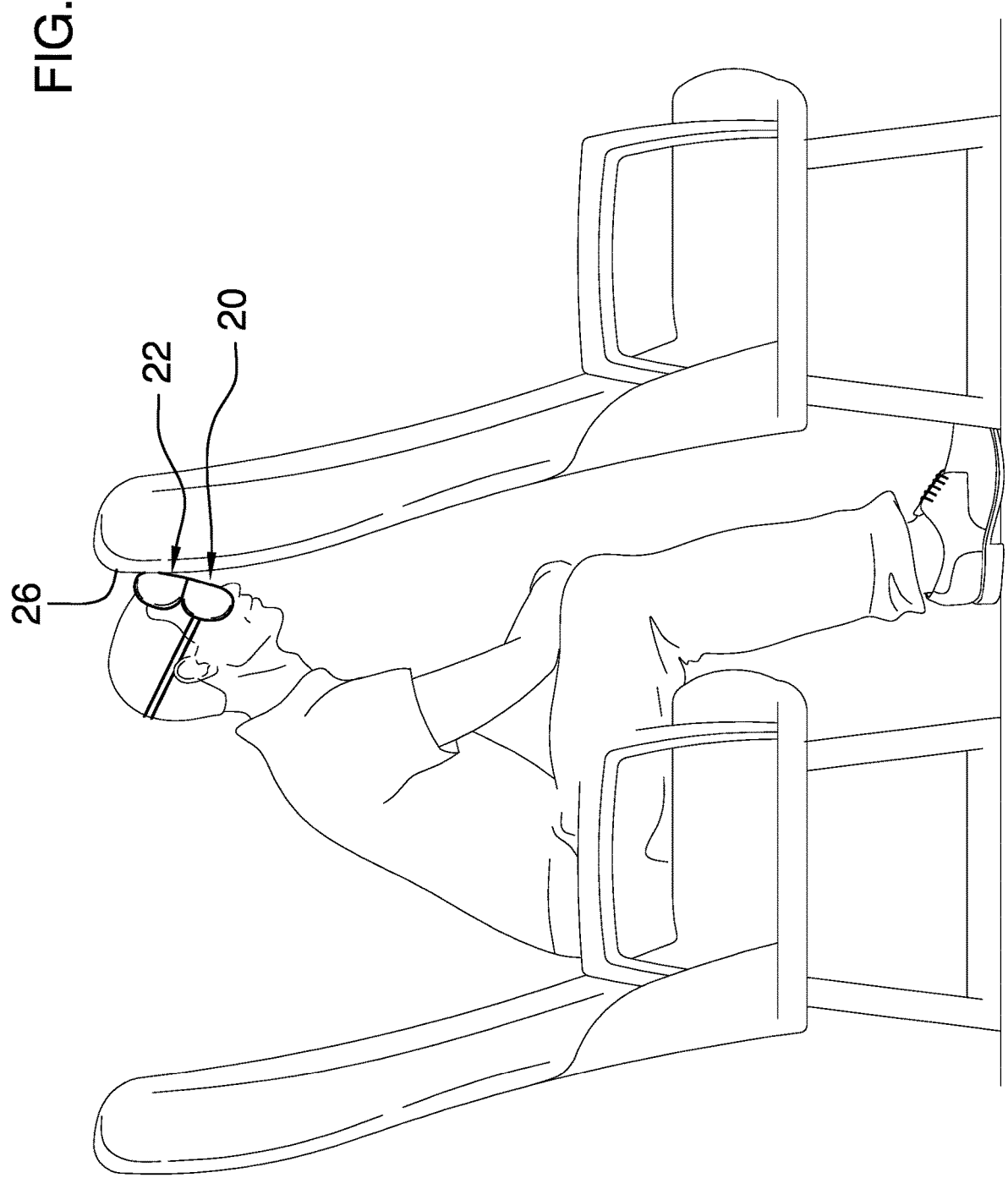

SLEEP MASK ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to sleep mask devices and more particularly pertains to a new sleep mask device for facilitating a user to rest their forehead against a support while sleeping in a seated position. The device includes a sleep mask which has a face portion and a flap portion which is foldable between a stored position and a deployed position. The flap portion rests on the user's forehead when the flap portion is positioned in the deployed position to cushion the user's forehead against the support.

(2) Description of Related Art Including Information Disclosed Under 37 CFR 1.97 and 1.98

The prior art relates to sleep mask devices including a sleep pillow device that includes a pair of lateral cushions each extending away from a central cushion. The prior art discloses a pillow device that includes a helmet being wearable on a user's head and a neck ring being attached to the helmet which extends partially around the user's neck. The prior art discloses a sleep mask device that includes a sleeve which insertably receives a weighted panel or a thermal panel. The prior art discloses an eye covering device that includes a band with a plurality of cells being distributed along the band and pair of flared ends. The prior art discloses a sleep pillow device that includes a pair of pillows that are positionable on opposing side of a user's head and a face panel which is attached to the pillows and which extends across the user's face. The prior art discloses a sleep enhancing device that comprises an elongated pillow that wraps around a user's eyes and ears.

BRIEF SUMMARY OF THE INVENTION

An embodiment of the disclosure meets the needs presented above by generally comprising a sleep mask that is wearable on a user's face such that the sleep mask covers the user's eyes. The sleep mask has a face portion and a flap portion. The face portion rests against the user's face when the sleep mask is worn. The flap portion is positionable in a deployed position has the flap portion resting against the user's forehead to facilitate the user to comfortably rest their forehead against a support object when the user is sleeping in a sitting position. The flap portion is positionable in a stored position having the flap portion resting against the face portion. A pair of elastomeric straps is each coupled to the sleep mask thereby facilitating the pair of elastomeric straps to be worn around the user's head for retaining the sleep mask on the user's face.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein:

FIG. 7 is a perspective in-use view of an embodiment of the disclosure showing a user leaning their forehead against a support.

DETAILED DESCRIPTION OF THE INVENTION

Figure 1:
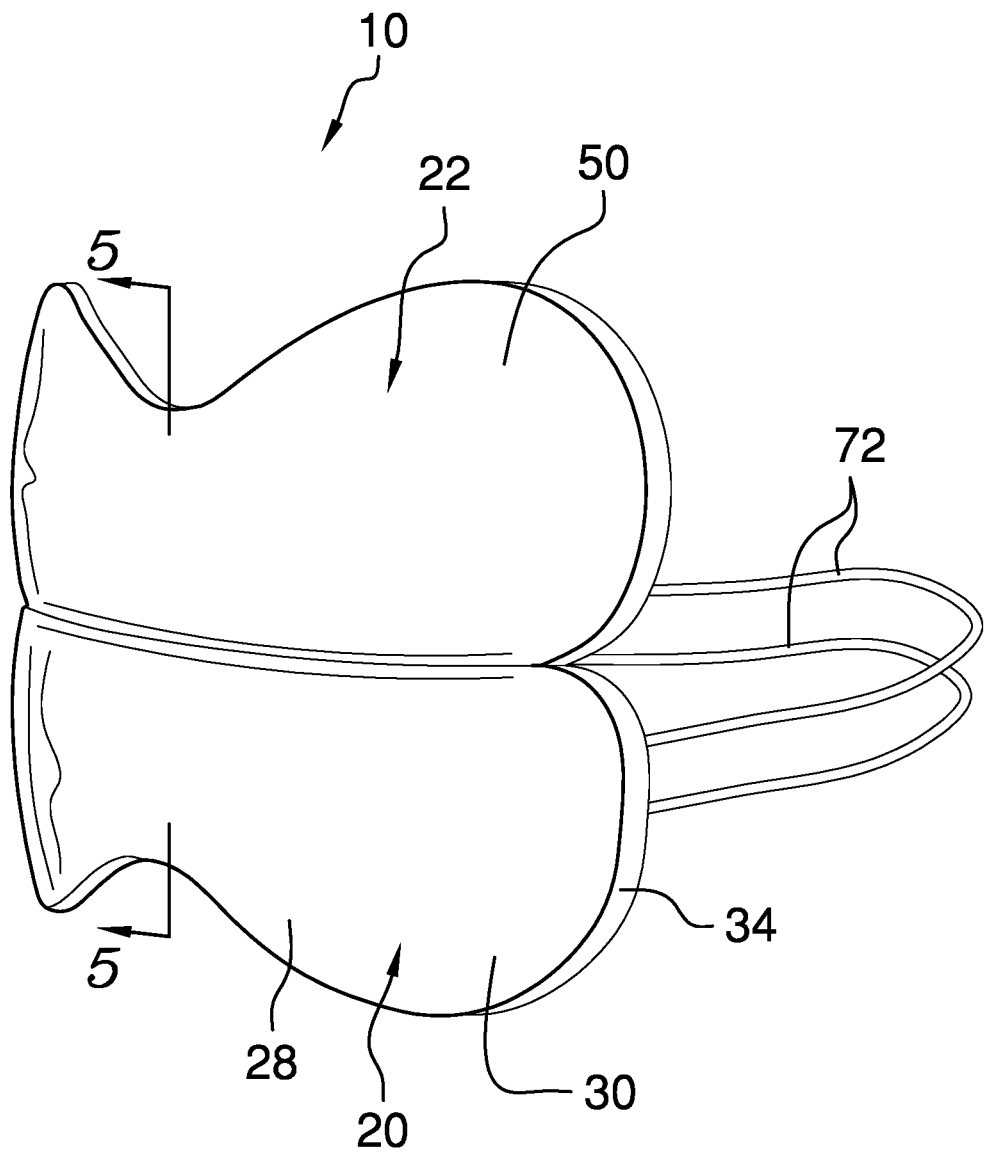
FIG. 1 is a front perspective view of a sleep mask assembly according to an embodiment of the disclosure.
Figure 2:
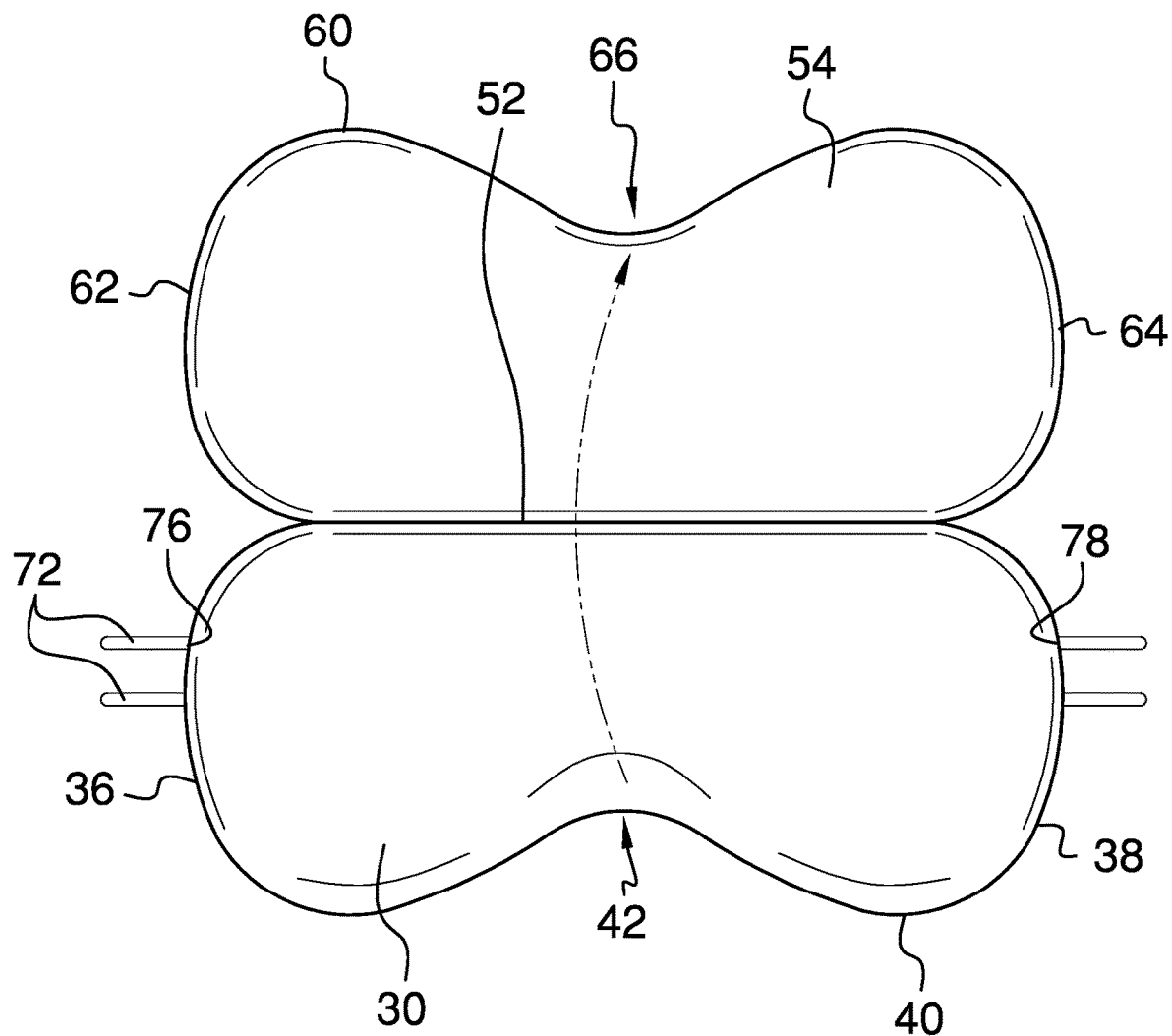
FIG. 2 is a front view of an embodiment of the disclosure.
Figure 3:
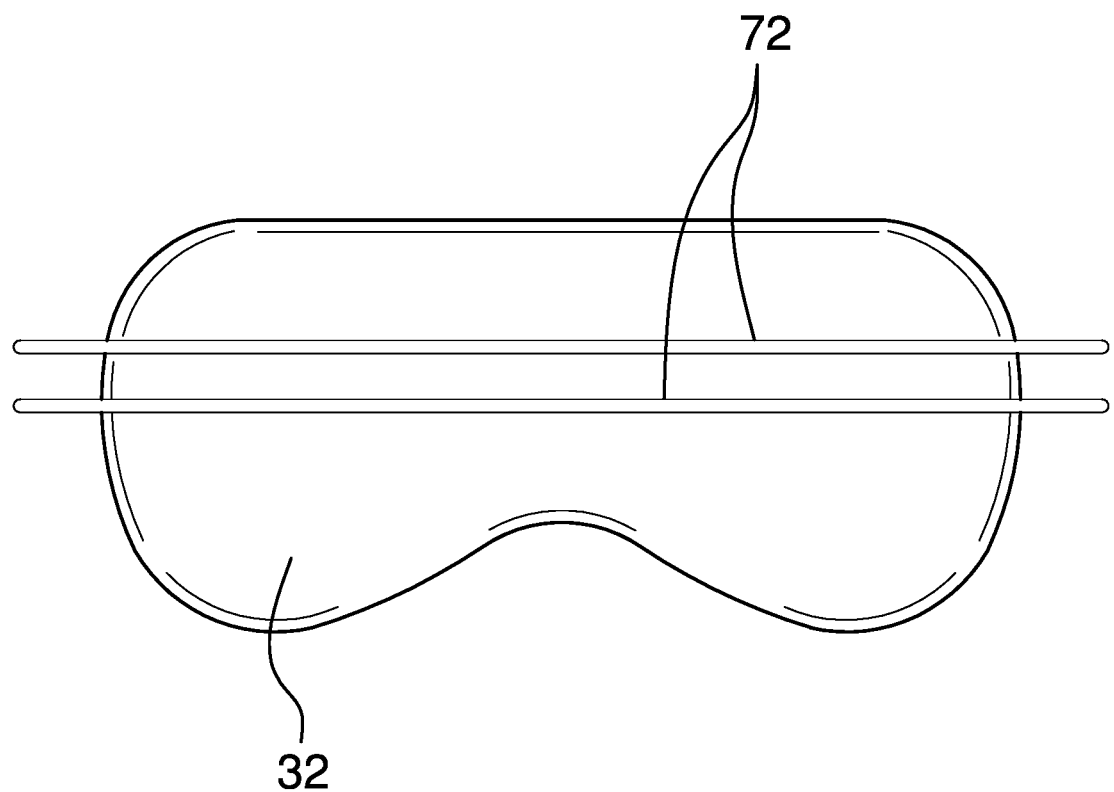
FIG. 3 is a back view of an embodiment of the disclosure.
Figure 4:
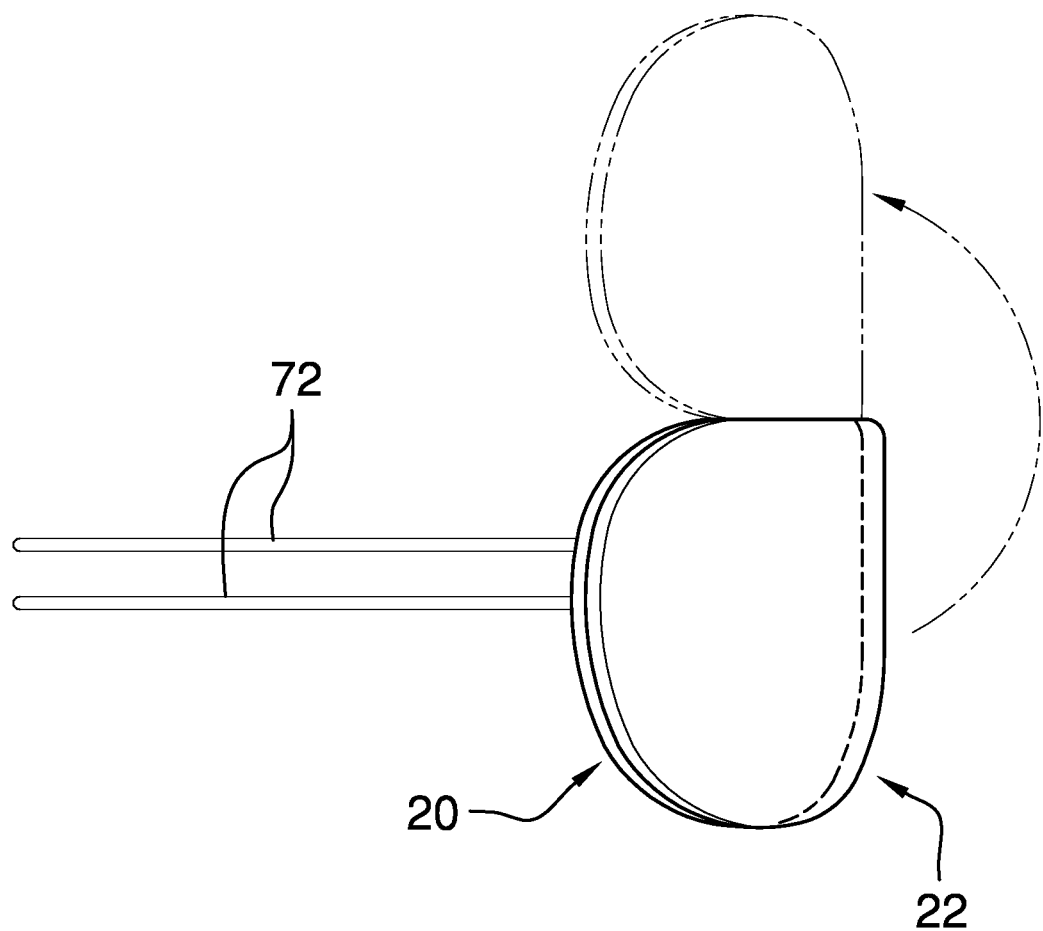
FIG. 4 is a right side view of an embodiment of the disclosure.
Figure 5:
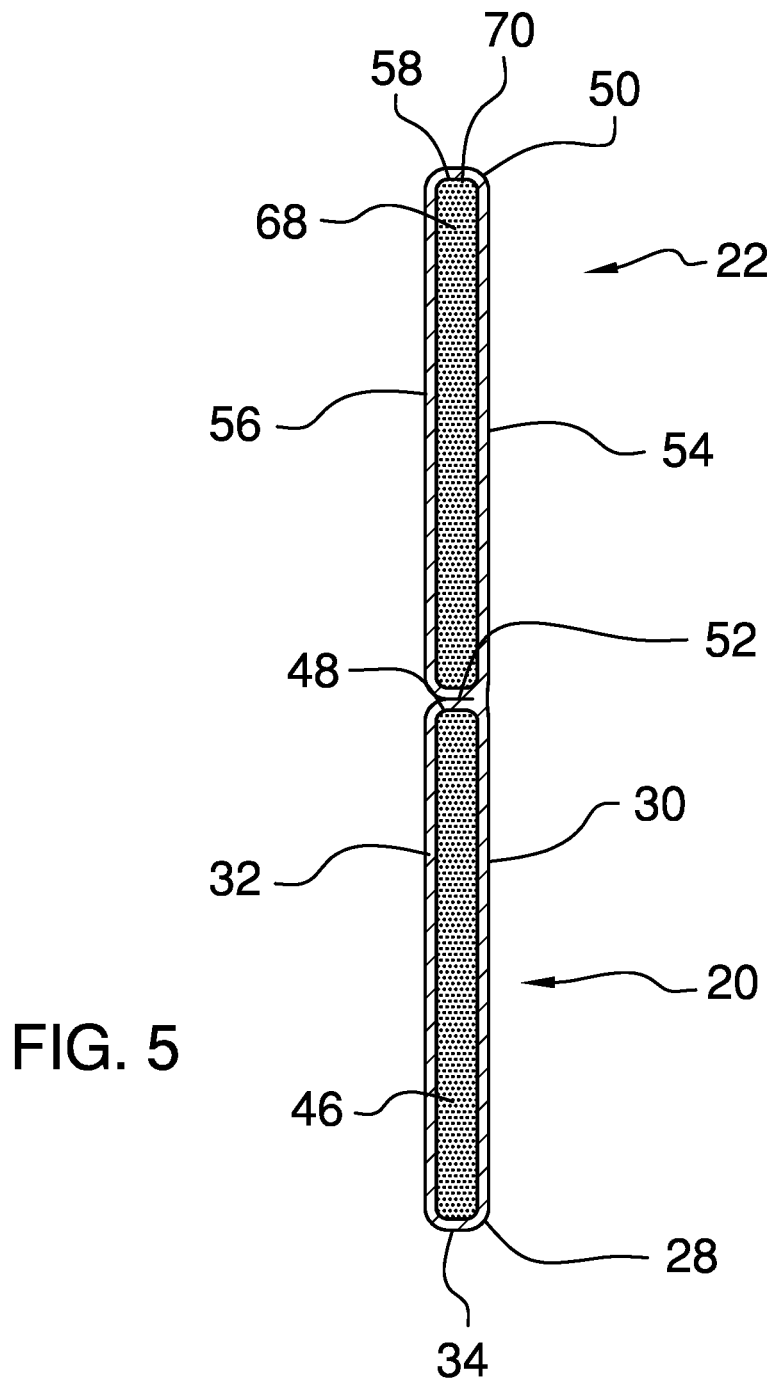
FIG. 5 is a cross sectional view taken along line 5-5 of FIG. 1 of an embodiment of the disclosure.
Figure 6:
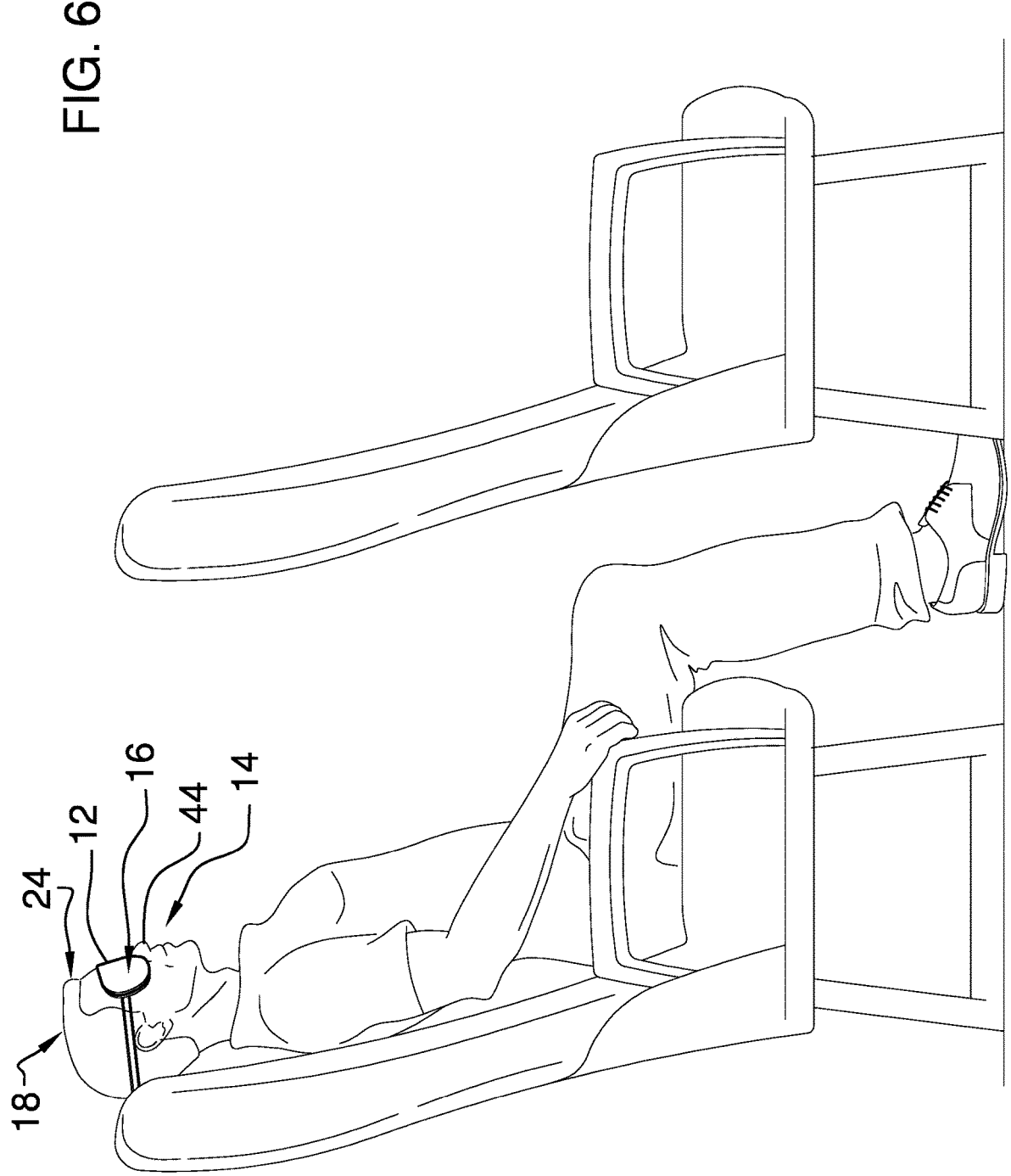
FIG. 6 is a perspective in-use view of an embodiment of the disclosure showing a user sleeping in a seated position.

With reference now to the drawings, and in particular to FIGS. 1 through 7 thereof, a new sleep mask device embodying the principles and concepts of an embodiment of the disclosure and generally designated by the reference numeral 10 will be described.

As best illustrated in FIGS. 1 through 7, the sleep mask assembly 10 generally comprises a sleep mask 12 that is wearable on a user's face 14 such that the sleep mask 12 covers the user's eyes 16. The sleep mask 12 is comprised of an opaque material to inhibit light from passing through the sleep mask 12 thereby enhancing the user's 18 ability to sleep during daylight hours. The sleep mask 12 has a face portion 20 and a flap portion 22. The face portion 20 rests against the user's face 14 when the sleep mask 12 is being worn by the user 18. The flap portion 22 is positionable in a deployed position having the flap portion 22 resting against the user's forehead 24. In this way the user 18 can comfortably rest their forehead 24 against a support object 26 when the user 18 is sleeping in a sitting position. The support object 26 may be the backrest of a seat that is located in front of the user 18 when the user 18 is seated in a commercial aircraft, a public transportation bus or other type of vehicle that would commonly involve the user 18 sleeping in a seated position. The flap portion 22 is positionable in a stored position having the flap portion 22 resting against the face portion 20.

The sleep mask 12 includes a first cover 28 that defines the face portion 20. The first cover 28 has a forward wall 30, a rearward wall 32 and a perimeter wall 34 extending between the forward wall 30 and the rearward wall 32. The perimeter wall 34 has a first lateral side 36, a second lateral side 38 and a bottom side 40 and each of the first lateral side 36 and the second lateral side 38 curves outwardly along a lateral axis extending between the first lateral side 36 and the second lateral side 38. The bottom side 40 curves upwardly a point that is centrally located between the first lateral side 36 and the second lateral side 38 to define a nose space 42 to accommodate the user's nose 44 when the sleep mask 12 is worn on the user's face 14. The sleep mask 12 includes a first pad 46 that is surrounded by the first cover 28. The first pad 46 has an outer surface 48 that is contoured to conform to the perimeter wall 34 of the first cover 28. The first pad 46 is comprised of a resiliently compressible material to enhance comfort for the user 18.

The sleep mask 12 includes a second cover 50 which defines the flap portion 22. The forward wall 30 of the first cover 28 extends beyond an upper threshold 52 of the face portion 20 such that the forward wall 30 defines a forward wall 54 of the second cover 50. The second cover 50 has a back wall 56 and a peripheral wall 58 extending between the forward wall 54 of the second cover 50 and the back wall 56. The peripheral wall 58 has an upper side 60, a first lateral side 62 and a second lateral side 64. Each of the first lateral side 62 and the second lateral side 64 of the peripheral wall 58 curves outwardly along a lateral axis extending between the first lateral side 62 and the second lateral side 64 of the peripheral wall 58.

The sleep mask 12 is foldable along the upper threshold 52 of the face portion 20 having the forward wall 54 of the second cover 50 resting against the forward wall 30 of the first cover 28 when the flap portion 22 is positioned in the stored position. The forward wall 30 of the second cover 50 lies on a plane that is oriented coplanar with the forward wall 30 of the first cover 28 when the flap portion 22 is positioned in the deployed position. The upper side 60 curves downwardly at a point that is centrally located between the first lateral side 62 and the second lateral side 64 of the peripheral wall 58 to define a nose space 66 in the flap portion 22. The nose space 66 in the flap portion 22 accommodates the user's nose 44 when the sleep mask 12 is worn on the user's face 14 and the flap portion 22 is positioned in the stored position. The sleep mask 12 includes a second pad 68 that is surrounded by the second cover 50. The second pad 68 has an outside surface 70 that is contoured to conform to the peripheral wall 58 of the second cover 50. Additionally, the second pad 68 is comprised of a resiliently compressible material to enhance comfort for the user 18.

A pair of elastomeric straps 72 is provided and each of the elastomeric straps 72 is coupled to the sleep mask 12 such that the pair of elastomeric straps 72 forms a closed loop with the sleep mask 12. The pair of elastomeric straps 72 can be worn around the user's head 74 for retaining the sleep mask 12 on the user's face 14. Each of the pair of elastomeric straps 72 has a first end 76 and a second end 78. The first end 76 of each of the elastomeric straps 72 is coupled to the first lateral side 36 of the perimeter wall 34 of the first cover 28. The second end 78 of each of the elastomeric straps 72 is coupled to the second lateral side 38 of the perimeter wall 34 of the first cover 28. Furthermore, the elastomeric straps 72 are spaced apart from each other and are vertically distributed on the first lateral side 36 and the second lateral side 38 of the perimeter wall 34 of the first cover 28.

In use, the sleep mask 12 is worn on the user's face 14 when the user 18 wishes to sleep during daylight hours. Furthermore, as is most clearly shown in FIG. 6, the flap portion 22 is positioned in the stored position when the user 18 is sleeping in a seated position while the user's head 74 is resting against a headrest 80 of a seat 82 in which the user 18 is seated. As is most clearly shown in FIG. 7, the flap portion 22 is positioned in the deployed position when the user 18 is sleeping in a seated position while the user 18 is leaning against a backrest 84 of a seat 86 that is in front of the seat 82 in which the user 18 is seated. In this way the flap portion 22 cushions the user's forehead 24 against the backrest 84 of the seat 86 to enhance comfort for the user 18.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

We claim:

1. A sleep mask assembly having a flap portion being foldable onto a user's forehead to facilitate the user to comfortably rest their forehead against a support, said assembly comprising:

a sleep mask being wearable on a user's face such that said sleep mask covers the user's eyes, said sleep mask being comprised of an opaque material wherein said sleep mask is configured to inhibit light from passing through said sleep mask thereby enhancing the user's ability to sleep during daylight hours, said sleep mask having a face portion and a flap portion, said face portion resting against the user's face when said sleep mask is being worn by the user, said flap portion being positionable in a deployed position having said flap portion resting against the user's forehead wherein said flap portion is configured to facilitate the user to comfortably rest their forehead against a support object when the user is sleeping in a sitting position, said flap portion being positionable in a stored position having said flap portion resting against said face portion;

a pair of elastomeric straps, each of said elastomeric straps being coupled to said sleep mask such that said pair of elastomeric straps forms a closed loop with said sleep mask thereby facilitating said pair of elastomeric straps to be worn around the user's head for retaining said sleep mask on the user's face;

wherein said sleep mask includes a first cover defining said face portion, said first cover having a forward wall, a rearward wall and a perimeter wall extending between said forward wall and said rearward wall, said perimeter wall having a first lateral side, a second lateral side and a bottom side, each of said first lateral side and said second lateral side curving outwardly along a lateral axis extending between said first lateral side and said second lateral side, said bottom side curving upwardly at a point being centrally located between said first lateral side and said second lateral side to define a nose space to accommodate the user's nose when said sleep mask is worn on the user's face; and wherein each of said pair of elastomeric straps has a first end and a second end, said first end of each of said elastomeric straps being coupled to said first lateral side of said perimeter wall of said first cover, said second end of each of said elastomeric straps being coupled to said second lateral side of said perimeter wall of said first cover, said pair of elastomeric straps being spaced apart from each other and being vertically distributed on said first lateral side and said second lateral side of said perimeter wall of said first cover.

2. The assembly according to claim 1, wherein said sleep mask includes a first pad being surrounded by said first cover, said first pad having an outer surface being contoured to conform to said perimeter wall of said first cover, said first pad being comprised of a resiliently compressible material to enhance comfort for the user.

3. A sleep mask assembly having a flap portion being foldable onto a user's forehead to facilitate the user to comfortably rest their forehead against a support, said assembly comprising:

a sleep mask being wearable on a user's face such that said sleep mask covers the user's eyes, said sleep mask being comprised of an opaque material wherein said sleep mask is configured to inhibit light from passing through said sleep mask thereby enhancing the user's ability to sleep during daylight hours, said sleep mask having a face portion and a flap portion, said face portion resting against the user's face when said sleep mask is being worn by the user, said flap portion being positionable in a deployed position having said flap portion resting against the user's forehead wherein said flap portion is configured to facilitate the user to comfortably rest their forehead against a support object when the user is sleeping in a sitting position, said flap portion being positionable in a stored position having said flap portion resting against said face portion;

a pair of elastomeric straps, each of said elastomeric straps being coupled to said sleep mask such that said pair of elastomeric straps forms a closed loop with said sleep mask thereby facilitating said pair of elastomeric straps to be worn around the user's head for retaining said sleep mask on the user's face;

wherein said sleep mask includes a first cover defining said face portion, said first cover having a forward wall, a rearward wall and a perimeter wall extending between said forward wall and said rearward wall, said perimeter wall having a first lateral side, a second lateral side and a bottom side, each of said first lateral side and said second lateral side curving outwardly along a lateral axis extending between said first lateral side and said second lateral side, said bottom side curving upwardly at a point being centrally located between said first lateral side and said second lateral side to define a nose space to accommodate the user's nose when said sleep mask is worn on the user's face; and wherein said sleep mask includes a second cover defining said flap portion, said forward wall of said first cover extending beyond an upper threshold of said face portion such that said forward wall defines a forward wall of said second cover, said second cover having a back wall and a peripheral wall extending between said forward wall of said second cover and said back wall, said peripheral wall having a upper side, a first lateral side and a second lateral side, each of said first lateral side and said second lateral side of said peripheral wall curving outwardly along a lateral axis extending between said first lateral side and said second lateral side of said peripheral wall.

4. The assembly according to claim 3, wherein said sleep mask is foldable along said upper threshold of said face portion having said forward wall of said second cover resting against said forward wall of said first cover when said flap portion is positioned in said stored position.

5. The assembly according to claim 3, wherein said forward wall of said second cover lies on a plane being oriented coplanar with said forward wall of said first cover when said flap portion is positioned in said deployed position.

6. The assembly according to claim 3, wherein said upper side curves downwardly at a point being centrally located between said first lateral side and said second lateral side of said peripheral wall to define a nose space in said second cover to accommodate the user's nose when said sleep mask is worn on the user's face and said flap portion is positioned in said stored position.

7. The assembly according to claim 3, wherein said sleep mask includes a second pad being surrounded by said second cover, said second pad having an outside surface being contoured to conform to said peripheral wall of said second cover, said second pad being comprised of a resiliently compressible material to enhance comfort for the user.

8. A sleep mask assembly having a flap portion being foldable onto a user's forehead to facilitate the user to comfortably rest their forehead against a support, said assembly comprising:

a sleep mask being wearable on a user's face such that said sleep mask covers the user's eyes, said sleep mask being comprised of an opaque material wherein said sleep mask is configured to inhibit light from passing through said sleep mask thereby enhancing the user's ability to sleep during daylight hours, said sleep mask having a face portion and a flap portion, said face portion resting against the user's face when said sleep mask is being worn by the user, said flap portion being positionable in a deployed position having said flap portion resting against the user's forehead wherein said flap portion is configured to facilitate the user to comfortably rest their forehead against a support object when the user is sleeping in a sitting position, said flap portion being positionable in a stored position having said flap portion resting against said face portion;

wherein said sleep mask includes a first cover defining said face portion, said first cover having a forward wall, a rearward wall and a perimeter wall extending between said forward wall and said rearward wall, said perimeter wall having a first lateral side, a second lateral side and a bottom side, each of said first lateral side and said second lateral side curving outwardly along a lateral axis extending between said first lateral side and said second lateral side, said bottom side curving upwardly at a point being centrally located between said first lateral side and said second lateral side to define a nose space to accommodate the user's nose when said sleep mask is worn on the user's face;

wherein said sleep mask includes a first pad being surrounded by said first cover, said first pad having an outer surface being contoured to conform to said perimeter wall of said first cover, said first pad being comprised of a resiliently compressible material to enhance comfort for the user;

wherein said sleep mask includes a second cover defining said flap portion, said forward wall of said first cover extending beyond an upper threshold of said face portion such that said forward wall defines a forward wall of said second cover, said second cover having a back wall and a peripheral wall extending between said forward wall of said second cover and said back wall, said peripheral wall having a upper side, a first lateral side and a second lateral side, each of said first lateral side and said second lateral side of said peripheral wall curving outwardly along a lateral axis extending between said first lateral side and said second lateral side of said peripheral wall;

wherein said sleep mask is foldable along said upper threshold of said face portion having said forward wall of said second cover resting against said forward wall of said first cover when said flap portion is positioned in said stored position, said forward wall of said second cover lying on a plane being oriented coplanar with said forward wall of said first cover when said flap portion is positioned in said deployed position, said upper side curving downwardly at a point being centrally located between said first lateral side and said second lateral side of said peripheral wall to define a nose space in said second cover to accommodate the user's nose when said sleep mask is worn on the user's face and said flap portion is positioned in said stored position;

wherein said sleep mask includes a second pad being surrounded by said second cover, said second pad having an outside surface being contoured to conform to said peripheral wall of said second cover, said second pad being comprised of a resiliently compressible material to enhance comfort for the user; and a pair of elastomeric straps, each of said elastomeric straps being coupled to said sleep mask such that said pair of elastomeric straps forms a closed loop with said sleep mask thereby facilitating said pair of elastomeric straps to be worn around the user's head for retaining said sleep mask on the user's face, each of said pair of elastomeric straps having a first end and a second end, said first end of each of said elastomeric straps being coupled to said first lateral side of said perimeter wall of said first cover, said second end of each of said elastomeric straps being coupled to said second lateral side of said perimeter wall of said first cover, said pair of elastomeric straps being spaced apart from each other and being vertically distributed on said first lateral side and said second lateral side of said perimeter wall of said first cover.

* * * * *